(12) United States Patent
Kong et al.

(10) Patent No.: US 12,035,990 B2
(45) Date of Patent: Jul. 16, 2024

(54) ENDOSCOPIC SURGERY ROBOT

(71) Applicant: ROEN Surgical, Inc., Daejeon (KR)

(72) Inventors: Duk Yoo Kong, Daejeon (KR); Un Je Yang, Daejeon (KR); Chang Kyun Kim, Daejeon (KR)

(73) Assignee: ROEN Surgical, Inc., Daejeon (KR)

( * ) Notice: Subject to any disclaimer, the term of this patent is extended or adjusted under 35 U.S.C. 154(b) by 263 days.

(21) Appl. No.: 17/400,060

(22) Filed: Aug. 11, 2021

(65) Prior Publication Data

US 2022/0331035 A1 Oct. 20, 2022

(30) Foreign Application Priority Data

Apr. 15, 2021 (KR) .......................... 10-2021-0049246

(51) Int. Cl.
| | |
|---|---|
| *A61B 34/00* | (2016.01) |
| *A61B 34/30* | (2016.01) |
| *B25J 9/04* | (2006.01) |
| *B25J 9/16* | (2006.01) |
| *A61B 17/29* | (2006.01) |

(52) U.S. Cl.
CPC .............. *A61B 34/70* (2016.02); *A61B 34/30* (2016.02); *A61B 34/71* (2016.02); *B25J 9/04* (2013.01); *B25J 9/1615* (2013.01); *A61B 2017/2908* (2013.01); *A61B 2017/2929* (2013.01); *A61B 2034/301* (2016.02)

(58) Field of Classification Search
CPC . A61B 34/71; A61B 17/29; A61B 2017/2908; A61B 2017/2929; A61B 34/30; A61B 34/70; A61B 2017/00318
See application file for complete search history.

(56) References Cited

U.S. PATENT DOCUMENTS

| | | |
|---|---|---|
| 2018/0214226 A1 | 8/2018 | Kan |
| 2019/0239966 A1 | 8/2019 | Xu et al. |
| 2020/0315645 A1 | 10/2020 | Kim et al. |

FOREIGN PATENT DOCUMENTS

| | | |
|---|---|---|
| KR | 101173619 | 8/2012 |
| KR | 20140104502 | 8/2014 |
| KR | 101938964 | 1/2019 |

OTHER PUBLICATIONS

Yang, et al., "surgical robot," Sep. 9, 2018, pp. 1-19 of English translation and pp. 44-59 of Figures (figure pages are marked 23-38 in original Korean application).*

* cited by examiner

*Primary Examiner* — Kathleen S Holwerda
*Assistant Examiner* — Daniel Icet
(74) *Attorney, Agent, or Firm* — JCIPRNET (57) ABSTRACT

A surgical robot includes a surgical tool including a bendable joint portion, and a bending tendon connected to the joint portion and configured to bend the joint portion, a tube connected to the surgical tool and configured to accommodate the bending tendon therein, a base housing configured to rotatably support the tube and accommodate the bending tendon that passes through the tube, a bending driver configured to grasp the bending tendon, and translate in a longitudinal direction parallel to a rotation axis of the tube with respect to the base housing, and a rotation driver configured to rotatably support the tube with respect to the base housing, wherein when the tube rotates, the rotation driver is connected to one portion of the bending driver that grasps the bending tendon, and rotates the tube and the bending tendon together.

12 Claims, 5 Drawing Sheets

ENDOSCOPIC SURGERY ROBOT

CROSS-REFERENCE TO RELATED APPLICATION(S)

This application claims the benefit of Korean Patent Application No. 10-2021-0049246, filed on Apr. 15, 2021, in the Korean Intellectual Property Office, the disclosure of which is incorporated herein by reference.

BACKGROUND

1. Field of the Invention

The following description relates to an endoscopic surgery robot.

2. Description of the Related Art

Surgical tools used in endoscopic surgery robots include, for example, multifunctional surgical forceps such as tweezers, tongs, and scissors provided at a distal end of a thin and long pipe.

The surgical tools are used for procedures and operations in many fields. A number of surgical tools including joints at distal ends have been developed to enable more free motions, and many of such joints are driven by pulling or pushing multiple strands of wire cables.

As such, a plurality of operating wires are connected to the outside for the joint motion and manipulation of a surgical tool. In this case, when the surgical tool performs a rotational motion by itself, the plurality of operating wires may twist producing friction, reducing the operability due to the tension changing as the length of the wires changes unintentionally, and deforming or damaging the operating wires.

In performing the manipulation and joint driving of the surgical tool, a mechanism that may prevent twists of a plurality of driving tendons (e.g., wires) and minimize the effect of each drive even when the surgical tool rotates is needed.

The above description has been possessed or acquired by the inventor(s) in the course of conceiving the present invention and is not necessarily an art publicly known before the present application is filed.

SUMMARY

An aspect provides an endoscopic surgery robot that may continuously rotate while preventing twists of internal driving tendons.

According to an aspect, there is provided a surgical robot including a surgical tool including a bendable joint portion, and a bending tendon connected to the joint portion and configured to bend the joint portion, a tube connected to the surgical tool and configured to accommodate the bending tendon therein, a base housing configured to rotatably support the tube and accommodate the bending tendon that passes through the tube, a bending driver configured to grasp the bending tendon, and translate in a longitudinal direction parallel to a rotation axis of the tube with respect to the base housing, and a rotation driver configured to rotatably support the tube with respect to the base housing, wherein when the tube rotates, the rotation driver is connected to one portion of the bending driver that grasps the bending tendon, and rotates the tube and the bending tendon together.

The base housing may include a first guide shaft extending in the longitudinal direction and configured to fixedly support the base housing, the bending driver may include a first driving block configured to slide along the first guide shaft, and a bending drive shaft extending in the longitudinal direction and configured to be screwed to the first driving block to translate the first driving block in the longitudinal direction, and the first driving block may include a first block hole formed at a position at which the bending tendon passes therethrough, and a first grasping block rotatably provided with respect to the first block hole and configured to be rotated by the rotation driver while grasping the bending tendon.

The rotation driver may include a rotary arm configured to rotatably grasp the tube with respect to the base housing, and a fixing shaft extending in the longitudinal direction from the rotary arm and penetrating through the first grasping block.

A rotation axis of the first grasping block with respect to the first driving block may be the same as a rotation axis of the rotary arm.

The bending tendon may have a configuration of a pair of tendons that extend corresponding to respective flexion directions of the joint portion, the first driving block may have a pair of configurations that are arranged to be spaced apart from each other along the first guide shaft and slide while grasping the pair of bending tendons, respectively, and the pair of first driving blocks may be threaded in opposite directions such that the bending drive shaft is screwed thereto.

The fixing shaft may penetrate through respective first grasping blocks of the pair of first driving blocks at the same time, and rotation axes of the respective first grasping blocks of the pair of first driving blocks may be the same as the rotation axis of the rotary arm.

The surgical tool may further include a manipulator configured to manipulate a tip of the surgical tool, and a manipulation tendon configured to perform an operation of the manipulator and extending from the manipulator to the base housing through the tube, wherein the surgical robot may further include a manipulation driver configured to grasp the manipulation tendon accommodated in the base housing, and translate in the longitudinal direction with respect to the base housing.

The base housing may further include a second guide shaft extending in the longitudinal direction and configured to fixedly support the base housing, the manipulation driver may include a second driving block configured to slide along the second guide shaft, and a manipulation drive shaft extending in the longitudinal direction and configured to be screwed to the second driving block to translate the second driving block in the longitudinal direction, and the second driving block may include a second block hole formed at a position at which the manipulation tendon passes therethrough, and a second grasping block rotatably provided with respect to the second block hole and connected to the fixing shaft while grasping the manipulation tendon.

The fixing shaft may penetrate through the first grasping block and the second grasping block at the same time, and rotation axes of the first grasping block and the second grasping block may be the same as the rotation axis of the rotary arm.

The first guide shaft and the second guide shaft may be radially spaced apart from each other having the same radius with respect to the rotation axis of the rotary arm, and when viewed along the rotation axis of the rotary arm, the first grasping block and the second grasping block may have circular shapes overlapping each other.

According to another aspect, there is provided a surgical robot including a surgical tool including a first joint portion and a second joint portion that are bendable in different directions, a first bending tendon configured to bend the first joint portion, and a second bending tendon configured to bend the second joint portion, a tube connected to the surgical tool and configured to accommodate the first bending tendon and the second bending tendon therein, a base housing configured to rotatably support the tube and accommodate a plurality of tendons that pass through the tube, a first bending driver configured to grasp the first bending tendon, and translate in a longitudinal direction parallel to a rotation axis of the tube with respect to the base housing, a second bending driver configured to grasp the second bending tendon, and translate in the longitudinal direction with respect to the base housing, and a rotation driver configured to rotatably support the tube with respect to the base housing, wherein when the tube rotates, the rotation driver is connected to (i) one portion of the first bending driver that grasps the first bending tendon and (ii) one portion of the second bending driver that grasps the second bending tendon, and rotates the tube together with the first bending tendon and the second bending tendon.

The base housing may include a first guide shaft and a second guide shaft extending in the longitudinal direction and radially spaced apart from each other having the same radius about the rotation axis of the tube to fixedly support the base housing, the first bending driver may include a first driving block configured to slide along the first guide shaft, and a first bending drive shaft extending in the longitudinal direction and configured to be screwed to the first driving block to translate the first driving block in the longitudinal direction, the second bending driver may include a second driving block configured to slide along the second guide shaft, and a second bending drive shaft extending in the longitudinal direction and configured to be screwed to the second driving block to translate the second driving block in the longitudinal direction, the first driving block may include a first block hole formed at a position at which the first bending tendon and the second bending tendon pass therethrough, and a first grasping block rotatably provided with respect to the first block hole and configured to be rotated by the rotation driver while grasping the first bending tendon, and the second driving block may include a second block hole formed at a position at which the second bending tendon passes therethrough, and a second grasping block rotatably provided with respect to the second block hole and configured to be rotated by the rotation driver while grasping the second bending tendon.

The rotation driver may include a rotary arm configured to rotatably grasp the tube with respect to the base housing, and a fixing shaft extending in the longitudinal direction from the rotary arm and penetrating the first grasping block and the second grasping block, and rotation axes of the first grasping block and the second grasping block may be the same as the rotation axis of the rotary arm.

When viewed along the rotation axis of the rotary arm, the first grasping block and the second grasping block may have circular shapes overlapping each other.

Additional aspects of example embodiments will be set forth in part in the description which follows and, in part, will be apparent from the description, or may be learned by practice of the disclosure.

According to example embodiments, a surgical robot may guarantee an independent operation that is not affected by each drive even when the rotation, joint motion (bending), and end portion manipulation of a surgical tool are performed at the same time, thereby driving the surgical tool more precisely and stably.

According to example embodiments, a surgical robot may rotate a plurality of tendons for controlling a surgical tool together while maintaining their state of arrangement even when the surgical tool is rotated, thereby preventing twists of the tendons caused by the rotation of the surgical tool. This indicates that the surgical tool has constant performance and the same operability regardless of the rotational direction of the surgical tool.

According to example embodiments, a surgical robot has a structure for rotating only a plurality of grasping blocks that relatively rotate by the medium of a bearing when a surgical tool is rotated through a rotation driver, and thus, only a relatively small rotation output that overcomes only the frictional force applied between the bearing and the grasping blocks is added. Therefore, a rotational force to be added in addition to a rotational driving force needed by the existing surgical tool may be ignored.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Hereinafter, example embodiments of the present disclosure will be described with reference to the accompanying drawings. Regarding the reference numerals assigned to the components in the drawings, it should be noted that the same components will be designated by the same reference numerals, wherever possible, even though they are shown in different drawings. Also, in the description of the example embodiments, detailed description of well-known related structures or functions will be omitted when it is deemed that such description will cause ambiguous interpretation of the present disclosure.

Also, in the description of the components, terms such as first, second, A, B, (a), (b) or the like may be used herein when describing components of the present disclosure. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 1:
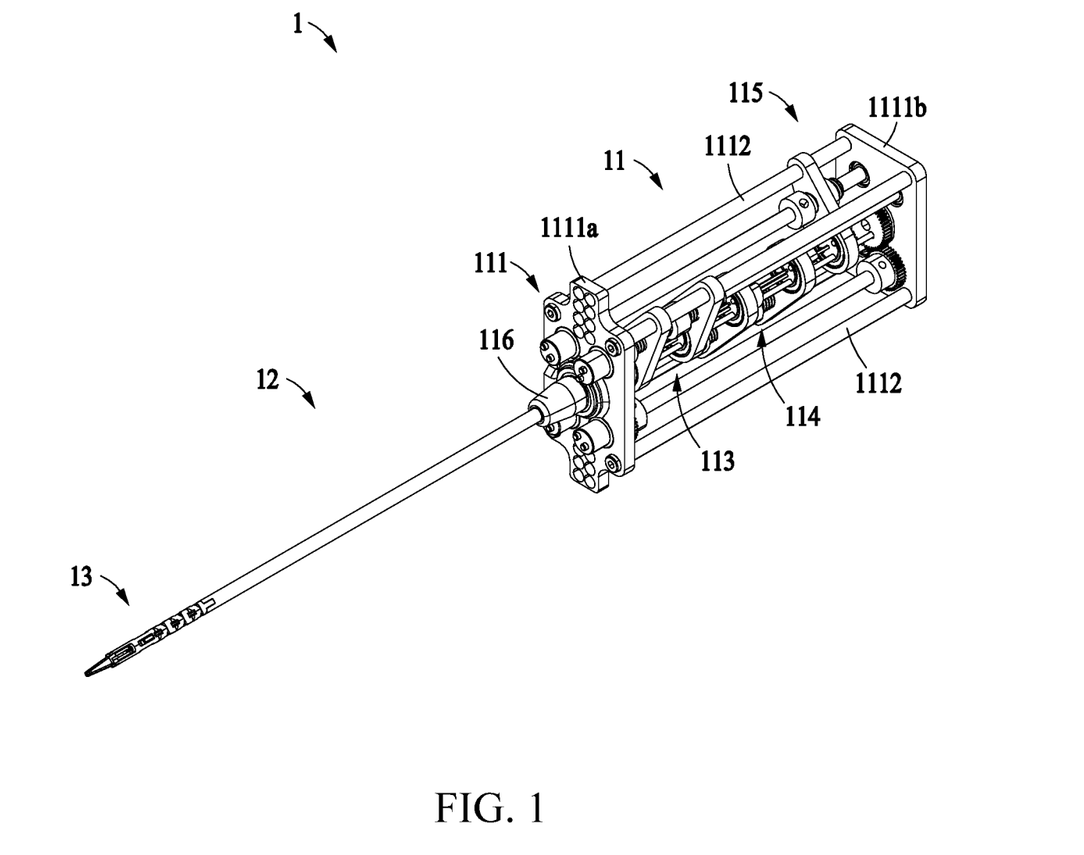
FIG. 1 is a front perspective view of a surgical robot according to an example embodiment.
Figure 2:
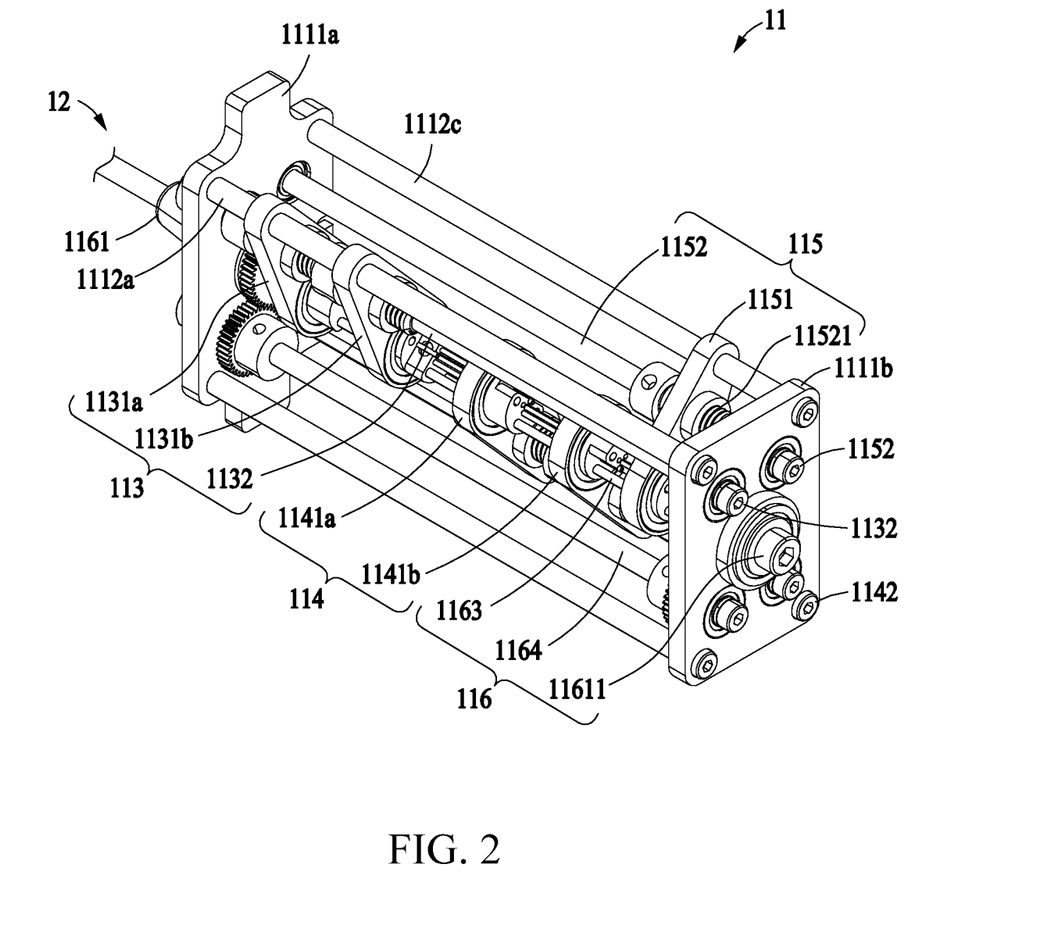
FIG. 2 is a rear perspective view of a surgical robot according to an example embodiment.
Figure 3:
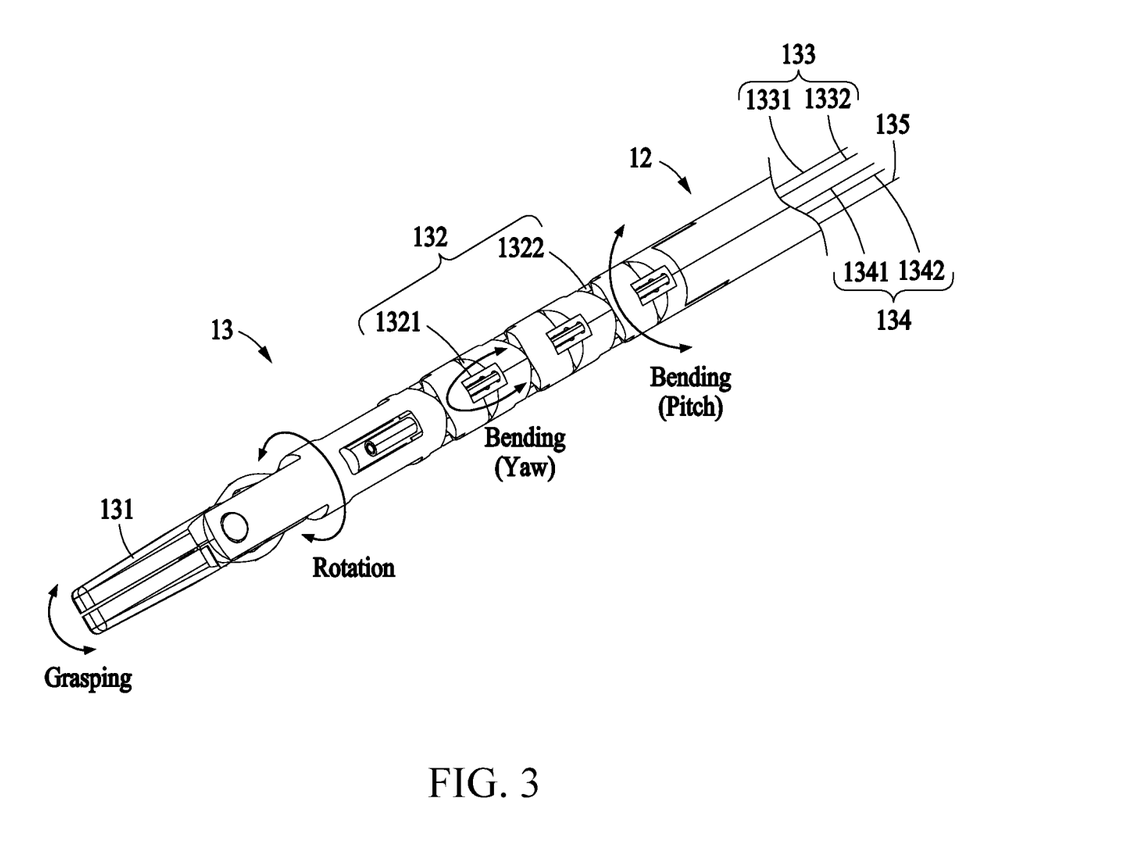
FIG. 3 is a perspective view of a surgical tool according to an example embodiment.
Figure 4:
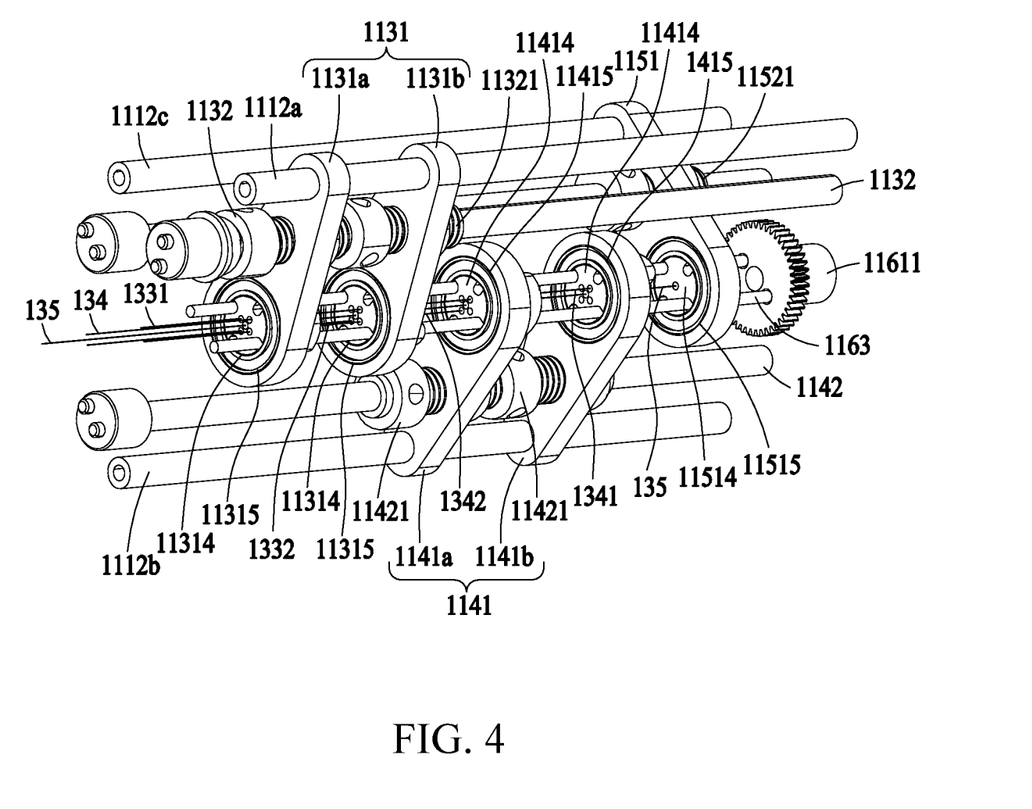
FIG. 4 is a perspective view illustrating the inside of a base housing according to an example embodiment.
Figure 5:
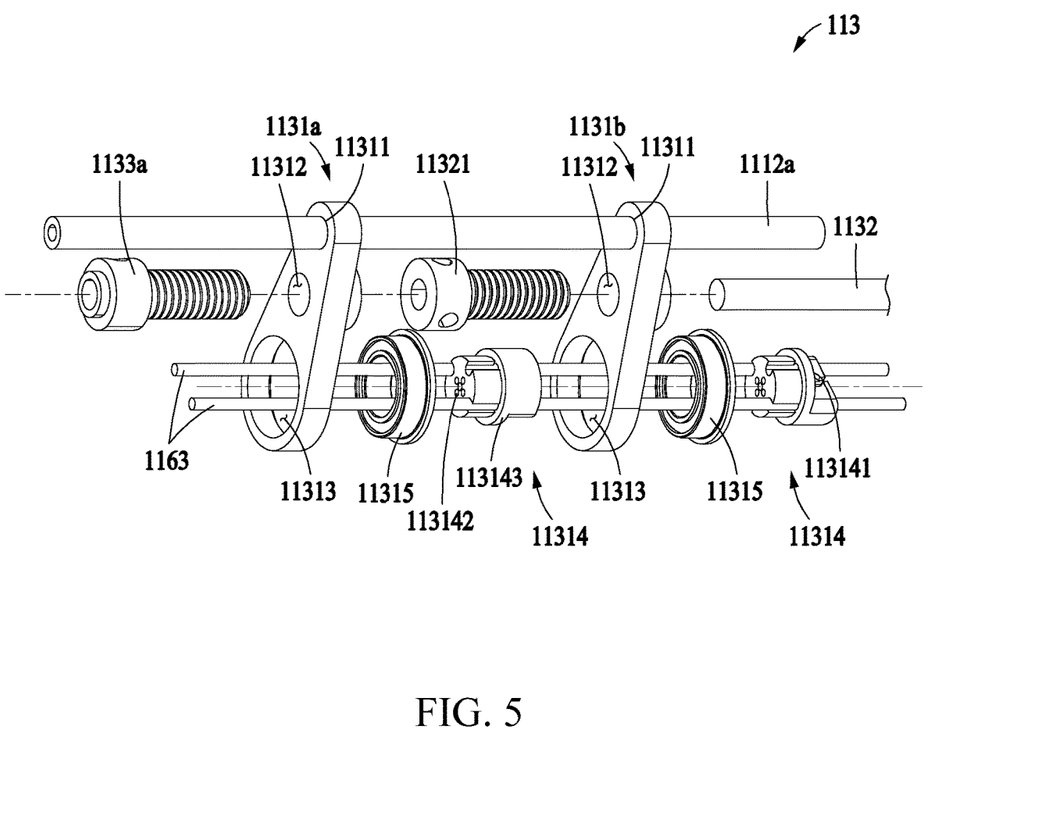
FIG. 5 is an exploded perspective view of a first bending driver according to an example embodiment.

FIG. 1 is a front perspective view of a surgical robot according to an example embodiment, FIG. 2 is a rear perspective view of the surgical robot according to an example embodiment, FIG. 3 is a perspective view of a surgical tool according to an example embodiment, FIG. 4 is a perspective view illustrating the inside of a base housing according to an example embodiment, and FIG. 5 is an exploded perspective view of a first bending driver according to an example embodiment.

Referring to FIGS. 1 to 5, a surgical robot 1 may control an operation of a surgical tool 13 capable of continuous axial rotation.

The surgical robot 1 may include the surgical tool 13, a tube 12 connected to the surgical tool 13 and extending therefrom, and a driver 11 for driving the tube 12 and the surgical tool 13.

The surgical tool 13 may include a manipulator 131 for performing grasping, crushing or cutting operation at a surgical tip provided at the end portion, a bending portion 132 that is bendable in at least one direction, bending tendons 133 and 134 for bending the bending portion 132, and a manipulation tendon 135 for performing an operation of the manipulator 131.

The manipulator 131 may be a tool provided at the end portion of the surgical tool 13 to perform manipulations on a surgical site. The manipulator 131 may be operated by a tension applied to the manipulation tendon 135.

For example, the manipulator 131 may include multifunctional surgical forceps such as tweezers, tongs, and scissors. Meanwhile, the example embodiments are not limited thereto. Unless otherwise stated, other types of surgical tools other than surgical forceps may be used.

The manipulation tendon 135 may extend rearward from the manipulator 131, pass through the tube 12 rearward, and be guided to a base housing 111.

For example, as the manipulation tendon 135 may be grasped by the manipulation driver 115 and translated in a longitudinal direction thereof, the manipulator 131 may be driven.

The bending portion 132 may include, for example, a first joint portion 1321 and a second joint portion 1322 that are bendable in different directions. In addition, the bending tendons 133 and 134 may include a first bending tendon 133 for bending the first joint portion 1321 and a second bending tendon 134 for bending the second joint portion 1322. Hereinafter, a case in which a two-degree-of-freedom (2-DOF) bending motion is possible is provided as an example, but unless otherwise stated, the scope of the present disclosure also includes a case in which only a 1-DOF bending motion is possible.

The first joint portion 1321 may be a joint that is bendable in one direction (e.g., yaw direction of FIG. 3) based on one rotation axis of the surgical tool 13 including the manipulator 131.

For example, the first joint portion 1321 may be bent based on one rotation axis by a tension applied to the first bending tendon 133 that is connected rearward.

The first bending tendon 133 may extend rearward from the first joint portion 1321, pass through the tube 12 rearward, and be guided to the base housing 111.

For example, the first joint portion 1321 may perform a flexion motion in both directions based on the rotation axis in a neutral state of being parallel to the tube 12. According to the above structure, the first bending tendon 133 may have a configuration of a pair of tendons that extend rearward corresponding to respective flexion directions of the first joint portion 1321.

For example, a pair of first bending tendons 133 may include one side 1331 and the other side 1332 that are guided to the base housing 111 through the tube 12 and grasped respectively through a pair of first grasping blocks 11314.

For example, the pair of first bending tendons 133 may be a configuration of an integral tendon that passes through the first joint portion 1321 and then is divided into two strands through the tube 12 and extends, or alternatively, a configuration of two tendons that separately extend from both edges for the respective flexion directions of the first joint portion 1321.

The second joint portion 1322 may be a joint that is bendable in a direction different from the direction in which the first joint portion 1321 is bendable. For example, the second joint portion 1322 may be bent in one direction (e.g., pitch direction of FIG. 3) based on one rotation axis by a tension applied to the second bending tendon 134 that is connected rearward.

The second bending tendon 134 may extend rearward from the second joint portion 1322, pass through the tube 12 rearward, and be guided to the base housing 111.

For example, the second joint portion 1322 may perform a flexion motion in both directions based on the rotation axis in a neutral state of being parallel to the tube 12. According to the above structure, the second bending tendon 134 may have a configuration of a pair of tendons that extend rearward corresponding to respective flexion directions of the second joint portion 1322.

For example, a pair of second bending tendons 134 may include one side 1341 and the other side 1342 that are guided to the base housing 111 through the tube 12 and grasped respectively through a pair of second grasping blocks 11414.

For example, the pair of second bending tendons 134 may be a configuration of an integral tendon that passes through the second joint portion 1322 and then is divided into two strands through the tube 12 and extends, or alternatively, a configuration of two tendons that separately extend from both edges for the respective flexion directions of the second joint portion 1322.

For example, the first joint portion 1321 and the second joint portion 1322 may have different rotation axes. For example, the rotation axes of the first joint portion 1321 and the second joint portion 1322 may be orthogonal to each other.

For example, as shown in FIG. 3, based on the direction in which the surgical tool 13 extends from the tube 12, the first joint portion 1321 may rotate the surgical tool 13 in yaw, and the second joint portion 1322 may rotate the surgical tool 13 in pitch.

The tube 12 may be a tubular member that extends rearward from the surgical tool 13 and includes an internal passage for accommodating a plurality of tendons.

The tube 12 may be rotatably provided in the base housing 111, and when the tube 12 is rotated about an axis parallel to the longitudinal direction by a rotation driver 116, the surgical tool 13 may be rotated together.

Herein, the term "longitudinal direction" refers to a direction parallel to the rotation axis on which a rotary arm 1161 rotatably grasping the tube 12 rotates.

The driver 11 may rotatably support the tube 12 and at the same time rotate the tube 12, and bend or manipulate the surgical tool 13 by translating the plurality of tendons 133, 134, and 135 passing through the tube 12 in the longitudinal direction.

For example, the driver 11 may include the base housing 111, a first bending driver 113, a second bending driver 114, a manipulation driver 115, and a rotation driver 116. The base housing 111 may rotatably support the tube 12.

The base housing 111 may drivably support the rotation driver 116.

For example, the base housing 111 may serve as a housing that fixes a rotation axis to enable rotation at a predetermined position such that the rotation driver 116 may grasp the tube 12 to rotate the tube 12 based on an axis parallel to the longitudinal direction. The base housing 111 may drivably support the manipulation driver 115, the first bending driver 113, and the second bending driver 114.

For example, the base housing 111 may guide a driving direction such that the drivers 113, 114, and 115 may grasp the plurality of tendons 133, 134, and 135, respectively, and translate in the longitudinal direction.

For example, the base housing 111 may include a front portion 1111a to which the tube 12 connected to the surgical tool 13 and extending rearward is connected, a rear portion 1111b spaced rearward apart from the front portion 1111a to face the front portion 1111a, and a plurality guide shafts 1112 extending in the longitudinal direction between the front portion 1111a and the rear portion 1111b and supporting the front portion 1111a and the rear portion 1111b.

The plurality of guide shafts 1112 may support the structure of the base housing 111 and at the same time guide the translation directions of the first bending driver 113, the second bending driver 114, and the manipulation driver 115.

For example, the plurality of guide shafts 1112 may be radially spaced apart from each other based on the rotation axis of the tube 12 when viewed along the rotation axis of the tube 12. For example, the plurality of guide shafts 1112a, 1112b, and 1112c may be radially spaced apart from each other in a state of having the same radius based on the rotation axis of the tube 12.

For example, the plurality of guide shafts 1112 may include a first guide shaft 1112a connected to the first bending driver 113 to guide the translation direction thereof, a second guide shaft 1112b connected to the second bending driver 114 to guide the translation direction thereof, and a third guide shaft 1112c connected to the manipulation driver 115 to guide the translation direction thereof.

The first bending driver 113 may bend the first joint portion 1321 by translating the first bending tendon 133 that passes through the tube 12 and is guided to the base housing 111 in the longitudinal direction.

For example, the first bending driver 113 may include a pair of first driving blocks 1131 that slide along the first guide shaft 1112a, and a first bending drive shaft 1132 that extends in the longitudinal direction and is screwed to the first driving block 1131 to translate the first driving block 1131 in the longitudinal direction.

The pair of first driving blocks 1131 may be provided to enclose the first guide shaft 1112a and spaced apart from each other along the first guide shaft 1112a, that is, in the longitudinal direction.

For example, each of the pair of first driving blocks 1131 may include a guide hole 11311 through which the first guide shaft 1112a passes, a threaded hole 11312 through which the first bending drive shaft 1132 passes and which is threaded on its inner side, a block hole 11313 provided to penetrate on a path through which the plurality of tendons pass, a first grasping block 11314 provided in the block hole 11313, and a bearing 11315 provided between the first grasping block 11314 and the block hole 11313.

For example, the driving directions of the pair of first driving blocks 1131 may be guided through the first guide shaft 1112a passing through the guide hole 11311, and the pair of first driving blocks 1131 may be translated in the longitudinal direction along the first guide shaft 1112a by the rotation of the first bending drive shaft 1132 screwed to the threaded hole 11312.

The first bending drive shaft 1132 may be rotated about a rotation axis parallel to the rotation axis of the tube 12 with respect to the base housing 111.

For example, the first bending drive shaft 1132 may include a screw member 11321 that is screwed to the threads of respective threaded holes 11312 of the pair of first driving blocks 1131 at portions at which the first bending driver shaft 1132 passes through the respective threaded holes 11312. For example, two screw members 11321 may be provided, and the description will be provided based on this example. However, the example embodiments are not limited thereto.

For example, the screw member 11321 may have a hollow that is fitted around the first bending drive shaft 1132, and an outer circumferential surface that is threaded. For example, the screw member 11321 may have a configuration that is detachably provided on the first bending drive shaft 1132.

The pair of first driving blocks 1131 may be threaded in opposite directions such that the first bending drive shaft 1132 is screwed thereto. According to this structure, only by rotating the first bending drive shaft 1132, the distance between the pair of first driving blocks 1131 may be increased or decreased, whereby the bending angle or the bending direction may be changed.

For example, the two screw members 11321 may be threaded in the same direction, while the threaded holes 11312 in the pair of first driving blocks 1131 may be threaded in opposite directions.

According to the above structure, the threads on the threaded holes 11312 in the pair of first driving blocks 1131, that engage with the screw members 1132, may be in opposite direction. Thus, when the first bending drive shaft 1132 is rotated, the pair of first driving blocks 1131 may move opposite to each other in the longitudinal direction. In other words, in response to the drive of the first bending drive shaft 1132, the distance between the pair of first driving blocks 1131 may be adjusted.

As another example, the threaded holes 11312 in the pair of first driving blocks 1131 may be threaded in the same direction, while the two screw members 11321 may be threaded in opposite directions.

As still another example, the screw member 11321 may not have a separate configuration that is provided in the first bending drive shaft 1132, but may have an integral structure in which the outer circumferential surface of the first bending drive shaft 1132 is threaded so as to be screwed to the respective threaded holes 11312 in the pair of first driving blocks 1131.

The first grasping block 11314 may be rotatably provided in the block hole 11313 of the first driving block 1131. The first grasping block 11314 may grasp the first bending tendon 133 and at the same time provide a path through which the other tendons pass.

For example, the bearing 11315 may be interposed between the first grasping block 11314 and the block hole 11313.

For example, the first grasping block 11314 may include a fixing portion 113141 that fixedly grasps the one side 1331 or the other side 1332 of the first bending tendon 133, a tendon path 113142 provided to penetrate such that the plurality of tendons 133, 134, and 135 pass, and a shaft fastener 113143 fixedly fastened to a fixing shaft 1633 of the rotation driver 116.

For example, each of the first grasping blocks 11314 of the pair of first driving blocks 1131a and 1131b may fixedly grasp the one side 1331 and the other side 1332 of the first bending tendon 133 that is divided into two strands and extends, through respective fixing portions 113141.

According to the above structure, the distance in the longitudinal direction between the pair of first grasping blocks 11314 grasping both sides 1331 and 1332 of the first bending tendon 133 may be decreased or increased in response to the rotation of the first bending drive shaft 1332, and consequently, the bending direction or the bending degree of the first joint portion 1321 to which the first bending tendon 133 is connected may be adjusted.

The plurality of tendon passages 113142 may provide a path through which the first bending tendon 133 and the second bending tendon 134 or the manipulation tendon 135 may all pass in parallel in the longitudinal direction.

For example, the plurality of tendon passages 113142 may be provided as a plurality of holes through which a plurality of strands of tendons may separately pass, which may facilitate the arrangement of the plurality of tendons and at the same time prevent interference among the tendons or their twists.

For example, the plurality of tendon passages 113142 may be provided at different positions based on the rotation axis, depending on the types of tendons.

For example, the central axis of the passage through which the manipulation tendon 135 passes, among the plurality of tendon passages 113142, may coincide with the rotation axis of the tube 12, and the passage through which the first bending tendon 133 or the second bending tendon 134 passes may be provided at a position radially spaced apart from the rotation axis of the tube 12.

As shown in FIGS. 1 to 5, the first bending driver 113 may have a configuration including a pair off driving blocks 1131a and 1131b that grasp both sides 1131 and 1132 of the two strands of first bending tendons 133, respectively. However, if the first joint portion 1321 is driven through a single strand of tendon, that is, if the first bending tendon 133 is a single strand of tendon extending to the base housing 111, the first drive block 1131 of the first bending driver 113 may have a single configuration that translates along the first guide shaft 1112a, rather than a pair of configurations.

The second bending driver 114 may bend the second joint portion 1322 by passing through the tube 12 and translating the second bending tendon 134 to the base housing 111 in the longitudinal direction.

For example, the first bending driver 113 and the second bending driver 114 may be provided at positions spaced apart from each other in the longitudinal direction.

As shown in FIGS. 2 and 3, the first bending driver 113 may have a configuration that is spaced frontward apart from the second bending driver 114. However, the example embodiments are not limited thereto. The first bending driver 113 and the second bending driver 114 may be provided at different positions.

For example, the second bending driver 114 may include a pair of second driving blocks 1141 that slide along the second guide shaft 1112b, and a second bending drive shaft 1142 that extends in the longitudinal direction and is screwed to the second driving block 1141 to translate the second driving block 1141 in the longitudinal direction.

For example, the second bending driver 114 may have the same configuration as the first bending driver 113, where the grasping tendon is changed to the second bending tendon 134, rather than the first bending tendon 133. Thus, the above description of the configuration of the first bending driver 113 may identically apply to the specific configuration and features of the second bending driver 114 with reference to FIGS. 3 and 4.

For example, similar to the first driving block 1131, each of the pair of second driving blocks 1141 may include a guide hole, a threaded hole, a block hole, a second grasping block 11414, and a bearing 11415. For example, similar to the first grasping block 11314, the second grasping block 11414 may include a fixing portion, a tendon passage, and a shaft fastener. For example, similar to the first bending drive shaft 1132, the second bending drive shaft 1142 may include a screw member 11421 that is screwed to the threads of respective threaded holes of the second driving blocks 1141 at portions at which the second bending drive shaft 1142 passes through the respective threaded holes.

The manipulation driver 115 may manipulate the end portion of the surgical tool 13 by translating the manipulation tendon 135 that passes through the tube 12 and is guided to the base housing 111 in the longitudinal direction.

For example, the manipulation driver 115 may be provided at a position spaced apart from the first bending driver 113 and the second bending driver 114 in the longitudinal direction. For example, the manipulation driver 115 may be provided at a position spaced rearward apart from the first bending driver 113 and the second bending driver 114, sequentially from the front in the longitudinal direction.

However, the order in which the first bending driver 113, the second bending driver 114, and the manipulation driver 115 are provided in the base housing 111 is not limited thereto, and the drivers 113, 114, and 115 may be provided at any positions unless their drive spaces according to drive displacement overlap each other.

For example, the manipulation driver 115 may include a third driving block 1151 that slides along the third guide shaft 1112c, and a manipulation drive shaft 1152 that extends in the longitudinal direction and is screwed to the third driving block 1151 to translate the third driving block 1151 in the longitudinal direction.

For example, while the first bending driver 113 may have a configuration that adjusts the relative distance, in the longitudinal direction, between both sides of the first bending tendon 133 that is divided into two strands and extends, the manipulation driver 115 may have a configuration that moves a single strand of the manipulation tendon 135 in the longitudinal direction.

For example, the manipulation driver 115 may have the same configuration as the first bending driver 113 described above, where the third driving block 1151 has a single configuration, rather than a pair of configurations, and the grasping tendon is changed to the manipulation tendon 135. For example, the third guide shaft 1112c may correspond to the first guide shaft 1112a, the third driving block 1151 may correspond to the first driving block 1131, and the manipulation drive shaft 1152 may correspond to the first bending drive shaft 1132. The above description of the configuration of the first bending driver 113 may identically apply to the specific configuration and features of the manipulation driver 115 with reference to FIGS. 3 and 4.

For example, similar to the first driving block 1131, the third driving block 1151 may include a guide hole, a threaded hole, a block hole, a third grasping block 11514, and a bearing 11515. For example, similar to the first grasping block 11314, the third grasping block 11514 may include a fixing portion, a tendon passage, and a shaft fastener. Meanwhile, if the third grasping block 11514 is positioned more rear than the other grasping blocks 11314 and 11414, the third grasping block 11514 may not include a tendon passage. For example, similar to the first bending drive shaft 1132, the manipulation drive shaft 1152 may include a screw member 11521 that is screwed to the threads of a threaded hole of the third driving block 1151 at a portion at which the manipulation drive shaft 1152 passes through the threaded hole.

For example, the rotation axes of the pair of first grasping blocks 11314 of the first bending driver 113, the pair of second grasping blocks 11414 of the second bending driver 114, and the third grasping block 11514 of the manipulation driver 115 may be the same as the rotation axis of the rotary arm 1161.

For example, when viewed along the rotation axis of the rotary arm 1161, the first grasping block 11314, the second grasping block 11414, and the third grasping block 11514 may all have circular shapes overlapping each other.

The rotation driver 116 may rotate relative to the base housing 111 in a state of grasping the tube 12 about the rotation axis, parallel to the longitudinal direction, of the tube 12.

For example, the rotation driver 116 may include the rotary arm 1161 that is rotatably provided relative to the base housing 111 in a state of grasping one side (e.g., end portion) of the tube 12 that extends rearward, a fixing shaft 1163 that extends in the longitudinal direction from the rotary arm 1161 and is coupled to the grasping blocks 11314, 11414, and 11514 of the plurality of drivers 113, 114, and 115, and a rotation drive shaft 1164 that is coupled to the rotary arm 1161 to rotate the rotary arm 1161.

The rotary arm 1161 may fixedly support, from the front, one side (e.g., end portion) of the tube 12 extending from the surgical tool 13. For example, the rotary arm 1161 may be rotatably provided in the front portion 1111a of the base housing 111.

The fixing shaft 1163 may extend in the longitudinal direction toward the rear of the rotary arm 1161 and be coupled to the pair of first grasping blocks 11314 of the first bending driver 113, the pair of second grasping blocks 11414 of the second bending driver 114, and the third grasping block 11514 of the manipulation driver 115.

For example, as shown in FIG. 4, the fixing shaft 1163 may have a configuration of a plurality of shafts that pass through the pair of first grasping blocks 11314, the pair of second grasping blocks 11414, and the third grasping block 11514 in the longitudinal direction.

In this case, the plurality of fixing shafts 1163 may include a configuration of at least two shafts that are radially spaced apart at the same interval based on the rotation axis of the rotary arm 1161.

For example, the fixing shaft 1163 may thus pass through shaft fasteners 113143 respectively provided in the pair of first grasping blocks 11314, the pair of second grasping blocks 11414, and the third grasping block 11514.

According to the above structure, the grasping blocks 11314, 11414, and 11514 of the plurality of drivers 113, 114, and 115 may maintain states of being arranged to all have the same rotation phase by the fixing shaft 1163, based on the rotation axis of the rotary arm 1161, and at the same time, rotational motions of the grasping blocks 11314, 11414, and 11514 of the plurality of drivers 113, 114, and 115 may be synchronized according to rotation, and thus, the states of arrangement of the plurality of tendons 133, 134, and 135 passing through the plurality of drivers 113, 114, and 115 may also be maintained.

For example, if the base housing 111 is separated into a front portion 1111a and a rear portion 1111b as shown in FIGS. 2 and 4, the rotary arm 1161 may further include, in the rear portion 1111b as well, a member 11611 that is fastened through the fixing shaft 1163 to relatively rotate, corresponding to a configuration that relatively rotates in a state of grasping the tube 12 in the front portion 1111a.

For example, the rotation drive shaft 1164 may extend in the longitudinal direction in the base housing 111 to transmit a rotational driving force to the rotary arm 1161.

For example, the rotation drive shaft 1164 may rotate the rotary arm 1161 through a power transmission element such as a gear, a pulley, or a belt.

For example, the rotation drive shaft 1164 may have a configuration that rotates the rotary arm 1161 by rotating the fixing shaft 1163, instead of being coupled directly to the rotary arm 1161.

According to example embodiments, the surgical robot 1 may guarantee an independent operation that is not affected by each drive even when the rotation, joint motion (bending), and end portion manipulation of the surgical tool 13 are performed at the same time, thereby driving the surgical tool 13 more precisely and stably.

According to example embodiments, the surgical robot 1 may also rotate the plurality of tendons 133, 134, and 135 for controlling the surgical tool 13 together while maintaining their state of arrangement even when the surgical tool 13 is rotated, thereby preventing twists of the tendons caused by the rotation of the surgical tool 13.

According to example embodiments, the surgical robot 1 may have a structure for rotating only the plurality of grasping blocks 11314, 11414, and 11514 that relatively rotate by the medium of the bearing 11315 when the surgical tool 13 is rotated through the rotation driver 116, thereby rotating the surgical tool 13 even with relatively small rotation output that overcomes only the frictional force applied between the bearing 11315 and the grasping blocks 11314, 11414, and 11514.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

What is claimed is:

1. A surgical robot comprising:
    a surgical tool comprising a bendable joint portion, and a bending tendon connected to the joint portion and configured to bend the joint portion;
    a tube connected to the surgical tool and configured to accommodate the bending tendon therein;
    a base housing configured to rotatably support the tube and accommodate the bending tendon that passes through the tube;
    a bending driver configured to grasp the bending tendon, and translate in a longitudinal direction parallel to a rotation axis of the tube with respect to the base housing; and a rotation driver configured to rotatably support the tube with respect to the base housing, wherein when the tube rotates, the rotation driver is connected to one portion of the bending driver that grasps the bending tendon, and rotates the tube and the bending tendon together,
wherein the base housing comprises:
a first guide shaft extending in the longitudinal direction and configured to fixedly support the base housing,
wherein the bending driver comprises:
a first driving block configured to slide along the first guide shaft; and
a bending drive shaft extending in the longitudinal direction, penetrating through the first driving block and configured to be screwed to the first driving block to translate the first driving block in the longitudinal direction,
wherein the first driving block comprises:
a first block hole formed at a position at which the bending tendon passes therethrough; and
a first grasping block rotatably provided with respect to the first block hole and configured to be rotated by the rotation driver while grasping the bending tendon.

2. The surgical robot of claim 1, wherein
the rotation driver comprises:
a rotary arm configured to rotatably grasp the tube with respect to the base housing; and
a fixing shaft extending in the longitudinal direction from the rotary arm and penetrating through the first grasping block.

3. The surgical robot of claim 2, wherein a rotation axis of the first grasping block with respect to the first driving block is the same as a rotation axis of the rotary arm.

4. The surgical robot of claim 2, wherein
the bending tendon has a configuration of a pair of tendons that extend corresponding to respective flexion directions of the joint portion,
the first driving block comprises a pair of first driving blocks that are arranged to be spaced apart from each other along the first guide shaft and slide while grasping the pair of bending tendons, respectively, and
the pair of first driving blocks are threaded in opposite directions such that the bending drive shaft is screwed thereto.

5. The surgical robot of claim 4, wherein
the fixing shaft penetrates through respective first grasping blocks of the pair of first driving blocks at the same time, and
rotation axes of the respective first grasping blocks of the pair of first driving blocks are the same as a rotation axis of the rotary arm.

6. The surgical robot of claim 2, wherein
the surgical tool further comprises:
a manipulator configured to manipulate a tip of the surgical tool; and
a manipulation tendon configured to perform an operation of the manipulator and extending from the manipulator to the base housing through the tube,
wherein the surgical robot further comprises:
a manipulation driver configured to grasp the manipulation tendon accommodated in the base housing, and translate in the longitudinal direction with respect to the base housing.

7. The surgical robot of claim 6, wherein
the base housing further comprises:
a second guide shaft extending in the longitudinal direction and configured to fixedly support the base housing,
the manipulation driver comprises:

a second driving block configured to slide along the second guide shaft; and
a manipulation drive shaft extending in the longitudinal direction and configured to be screwed to the second driving block to translate the second driving block in the longitudinal direction, and
the second driving block comprises:
a second block hole formed at a position at which the manipulation tendon passes therethrough; and
a second grasping block rotatably provided with respect to the second block hole and connected to the fixing shaft while grasping the manipulation tendon.

8. The surgical robot of claim 7, wherein
the fixing shaft penetrates through the first grasping block and the second grasping block at the same time, and
rotation axes of the first grasping block and the second grasping block are the same as a rotation axis of the rotary arm.

9. The surgical robot of claim 8, wherein
the first guide shaft and the second guide shaft are radially spaced apart from each other and have the same radius with respect to the rotation axis of the rotary arm, and
when viewed along the rotation axis of the rotary arm, the first grasping block and the second grasping block have circular shapes overlapping each other.

10. A surgical robot comprising:
a surgical tool comprising a first joint portion and a second joint portion that are bendable in different directions, a first bending tendon configured to bend the first joint portion, and a second bending tendon configured to bend the second joint portion;
a tube connected to the surgical tool and configured to accommodate the first bending tendon and the second bending tendon therein;
a base housing configured to rotatably support the tube and accommodate a plurality of tendons that pass through the tube;
a first bending driver configured to grasp the first bending tendon, and translate in a longitudinal direction parallel to a rotation axis of the tube with respect to the base housing;
a second bending driver configured to grasp the second bending tendon, and translate in the longitudinal direction with respect to the base housing; and
a rotation driver configured to rotatably support the tube with respect to the base housing, wherein when the tube rotates, the rotation driver is connected to (i) one portion of the first bending driver that grasps the first bending tendon and (ii) one portion of the second bending driver that grasps the second bending tendon, and rotates the tube together with the first bending tendon and the second bending tendon,
wherein the base housing comprises:
a first guide shaft and a second guide shaft extending in the longitudinal direction and radially spaced apart from each other having the same radius about the rotation axis of the tube to fixedly support the base housing,
wherein the first bending driver comprises:
a first driving block configured to slide along the first guide shaft; and
a first bending drive shaft extending in the longitudinal direction, penetrating through the first driving block and configured to be screwed to the first driving block to translate the first driving block in the longitudinal direction,
wherein the second bending driver comprises:

a second driving block configured to slide along the second guide shaft; and a second bending drive shaft extending in the longitudinal direction and configured to be screwed to the second driving block to translate the second driving block in the longitudinal direction, wherein the first driving block comprises:

a first block hole formed at a position at which the first bending tendon and the second bending tendon pass therethrough, and a first grasping block rotatably provided with respect to the first block hole and configured to be rotated by the rotation driver while grasping the first bending tendon, and the second driving block comprises:

a second block hole formed at a position at which the second bending tendon passes therethrough, and a second grasping block rotatably provided with respect to the second block hole and configured to be rotated by the rotation driver while grasping the second bending tendon.

11. The surgical robot of claim 10, wherein
the rotation driver comprises:
a rotary arm configured to rotatably grasp the tube with respect to the base housing; and
a fixing shaft extending in the longitudinal direction from the rotary arm and penetrating the first grasping block and the second grasping block, and
rotation axes of the first grasping block and the second grasping block are the same as a rotation axis of the rotary arm.

12. The surgical robot of claim 11, wherein when viewed along the rotation axis of the rotary arm, the first grasping block and the second grasping block have circular shapes overlapping each other.

* * * * *